US009820691B2

United States Patent
Kiani (10) Patent No.: US 9,820,691 B2
(45) Date of Patent: *Nov. 21, 2017

(54) FLUID TITRATION SYSTEM (75) Inventor: Massi E. Kiani, Laguna Niguel, CA (US)

(73) Assignee: MASIMO CORPORATION, Irvine, CA (US)

( * ) Notice: Subject to any disclaimer, the term of this patent is extended or adjusted under 35 U.S.C. 154(b) by 322 days.

This patent is subject to a terminal disclaimer.

(21) Appl. No.: 13/287,060

(22) Filed: Nov. 1, 2011

(65) Prior Publication Data

US 2012/0046557 A1    Feb. 23, 2012

Related U.S. Application Data

(63) Continuation of application No. 12/208,998, filed on Sep. 11, 2008, now Pat. No. 8,048,040.

(60) Provisional application No. 60/993,584, filed on Sep. 13, 2007.

(51) Int. Cl.
| | | |
|---|---|---|
| A61B 5/00 | (2006.01) | |
| A61B 5/0295 | (2006.01) | |
| A61B 5/1455 | (2006.01) | |
| A61M 5/142 | (2006.01) | |

(52) U.S. Cl.
CPC .......... *A61B 5/6826* (2013.01); *A61B 5/0295* (2013.01); *A61B 5/14551* (2013.01); *A61B 5/6838* (2013.01); *A61M 5/142* (2013.01); *A61M 2205/3306* (2013.01); *A61M 2205/3313* (2013.01)

(58) Field of Classification Search
CPC .. A61M 2205/3306; A61M 2205/3313; A61M 5/142; A61B 5/14551; A61B 5/6826; A61B 5/6838; A61B 5/0295; A61B 5/0806
USPC .............................................. 604/65–67, 503
See application file for complete search history.

(56) References Cited

U.S. PATENT DOCUMENTS

| | | |
|---|---|---|
| 4,109,643 A | 8/1978 | Bond et al. |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,111,817 A | 5/1992 | Clark et al. |
| 5,163,438 A | 11/1992 | Gordon et al. |
| 5,337,744 A | 8/1994 | Branigan |

(Continued)

*Primary Examiner* — Bhisma Mehta
*Assistant Examiner* — Larry R Wilson
(74) *Attorney, Agent, or Firm* — Knobbe, Martens, Olson & Bear LLP (57) ABSTRACT

A fluid titration system has an optical sensor, a physiological monitor, a titration controller and an infusion device. The optical sensor transmits multiple wavelengths of light into a tissue site of a person and detects the optical radiation after attenuation by pulsatile blood flowing within the tissue site. The physiological monitor receives a resulting sensor signal and derives a plethysmograph that corresponds to the pulsatile blood flow. The monitor also calculates a plethysmograph variability measure that is responsive to changes in perfusion at the tissue site. A titration controller generates a fluid control output according to the variability measure. The infusion device administers a liquid solution via an intravenous (IV) connection to the person according to the fluid control output so as to regulate at least one of a fluid flow start, rate and stop.

20 Claims, 8 Drawing Sheets

(56) References Cited

U.S. PATENT DOCUMENTS

| | | |
|---|---|---|
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,766,127 A | 6/1998 | Pologe et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,862,805 A * | 1/1999 | Nitzan ............... A61B 5/02416 128/898 |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,984,893 A * | 11/1999 | Ward ............... A61M 5/16827 128/DIG. 12 |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,165,151 A * | 12/2000 | Weiner ............... A61M 5/16813 604/250 |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |

(56) References Cited

U.S. PATENT DOCUMENTS

| | | |
|---|---|---|
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,201,734 B2 | 4/2007 | Hickle |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 2005/0177096 A1 | 8/2005 | Bollish et al. |
| 2007/0032732 A1* | 2/2007 | Shelley .............. A61B 5/0059 600/504 |
| 2007/0055198 A1* | 3/2007 | O'Mahony ....... A61M 5/14212 604/67 |
| 2008/0067132 A1* | 3/2008 | Ross .................. A61B 5/02007 210/739 |

* cited by examiner

FLUID TITRATION SYSTEM

REFERENCE TO RELATED APPLCATION

The present application claims priority benefit under 35 U.S.C. §120 to, and is a continuation of U.S. patent application Ser. No. 12/208,998, filed on Sep. 11, 2008, entitled "Fluid Titration System," now U.S. Pat. No. 8,048,040, which claims priority benefit under 35 U.S.C. §119 (e) from U.S. Provisional application No. 60/993,584, filed Sep. 13, 2007, entitled "Fluid Titration System,"which is incorporated herein by reference.

BACKGROUND OF THE INVENTION

Figure 1:
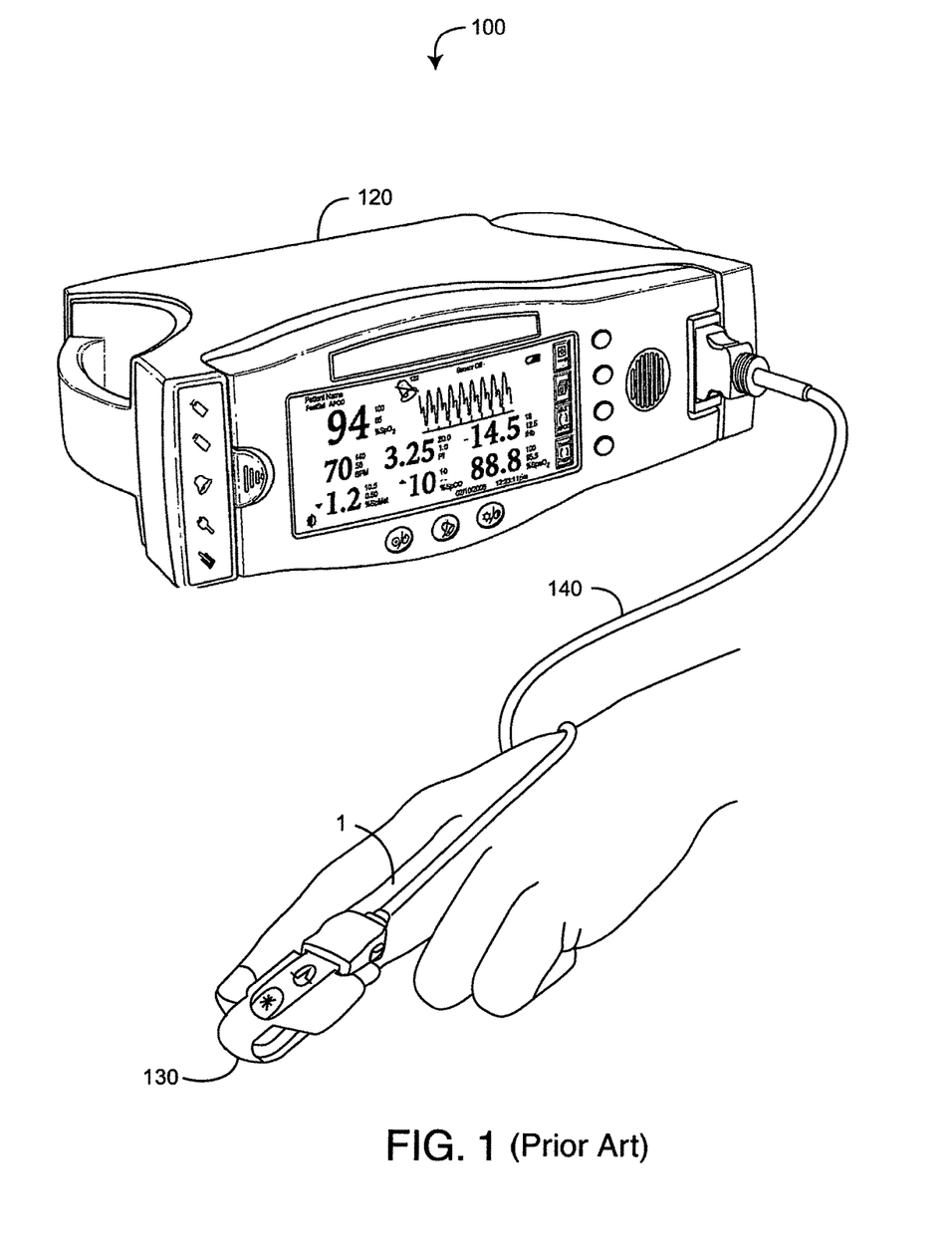
FIG. 1 is an illustration of a physiological monitoring system.

FIG. 1 illustrates a physiological monitoring system 100 having a physiological monitor 120, a noninvasive sensor 130 attached to a tissue site 1, and a sensor cable 140 interconnecting the monitor 120 and the sensor 130. Physiological monitoring systems for measuring constituents of circulating blood have gained rapid acceptance in a wide variety of medical applications, including surgical wards, intensive care and neonatal units, general wards, home care, physical training, and virtually all types of monitoring scenarios. The noninvasive sensor 130 has light emitting diodes (LEDs) and a detector. The LEDs transmit optical radiation into the tissue site 1, and the detector responds to the intensity of the optical radiation after absorption by pulsatile blood flow within the tissue site. Based upon this response, the physiological monitor 120 determines measurements for physiological parameters. The physiological monitoring system 100 may incorporate pulse oximetry, which is a widely accepted noninvasive procedure for measuring physiological parameters, such as oxygen saturation and pulse rate among others. The physiological monitoring system 100 may also incorporate advanced features, such as a multiple wavelength sensor and advanced processes for determining other physiological parameters, such as carboxyhemoglobin, methemoglobin and total hemoglobin, as a few examples. The physiological monitor 120 displays the physiological parameters and typically provides visual and audible alarm mechanisms that alert a caregiver when these parameters are outside of predetermined limits.

Pulse oximeters capable of reading through motion induced noise are disclosed in at least U.S. Pat. Nos. 6,770,028, 6,658,276, 6,650,917, 6,157,850, 6,002,952, 5,769,785, and 5,758,644; low noise pulse oximetry sensors are disclosed in at least U.S. Pat. No. 6,088,607 and 5,782,757; all of which are assigned to Masimo Corporation, Irvine, Calif. ("Masimo") and are incorporated by reference herein.

Physiological monitors and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208 [11,367,033], filed Mar. 1, 2006 and entitled Noninvasive Multi-Parameter Patient Monitor, both assigned to Masimo Laboratories, Irvine, Calif. (Masimo Labs) and both incorporated by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-5™, Rad-5v™ or PPO+™ Masimo SET® pulse oximeters, are all available from Masimo. Physiological monitoring systems including multiple wavelength sensors and corresponding noninvasive blood parameter monitors, such as Rainbow™ adhesive and reusable sensors and RAD-57™ and Radical-7™ monitors for measuring $SpO_2$, pulse rate, perfusion index, signal quality, HbCO and HbMet among other parameters are also available from Masimo.

Figure 2:
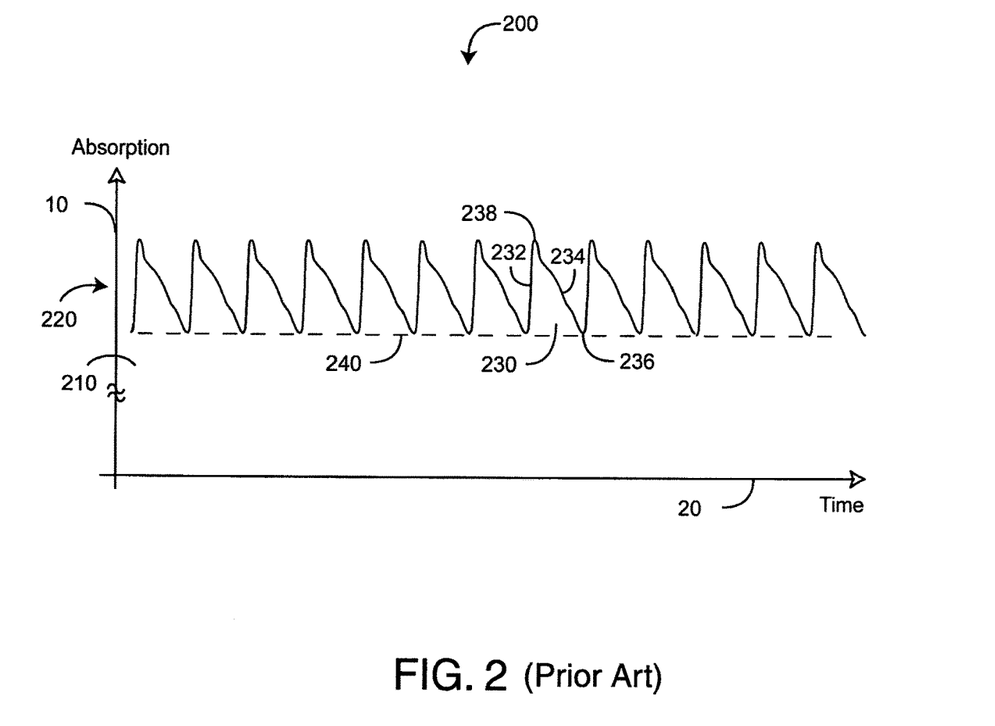
FIG. 2 is an absorption versus time graph of a standard pulse oximeter plethysmograph.

FIG. 2 illustrates the standard plethysmograph waveform 200, which can be derived from a pulse oximetry system, as described above. The plethysmograph waveform 200 illustrates light absorption at the tissue site, shown along the y-axis 10, versus time, shown along the x-axis 20. The total absorption includes components of static absorption 210 and variable absorption 220. Static absorption 210 is due to tissue, venous blood and a base volume of arterial blood. Variable absorption 220 is due to the pulse-added volume of arterial blood. That is, the plethysmograph waveform 200 is a visualization of the tissue site arterial blood volume change over time, and is a function of heart stroke volume, pressure gradient, arterial elasticity and peripheral resistance. The ideal waveform pulse 230 displays a broad peripheral flow curve, with a short, steep inflow phase 232 followed by a 3 to 4 times longer outflow phase 234. The inflow phase 232 is the result of tissue distention by the rapid blood volume inflow during ventricular systole. During the outflow phase 234, blood flow continues into the vascular bed during diastole. The plethysmograph baseline 240 indicates the minimum basal tissue perfusion.

SUMMARY OF THE INVENTION

Figure 3:
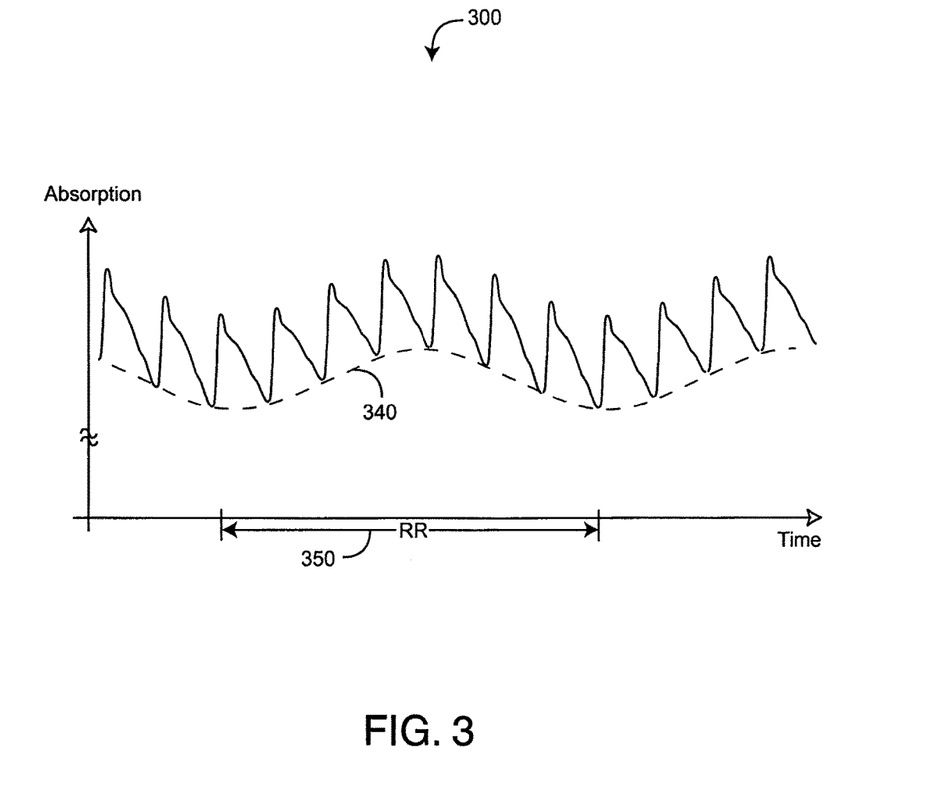
FIG. 3 is an absorption versus time graph of a plethysmograph exhibiting a respiration-induced, baseline cyclical variation.

FIG. 3 illustrates a hypovolemic plethysmograph waveform 300, i.e. a plethysmograph displaying characteristics of a person having an abnormal decrease in blood volume. Hypovolemia is often caused from blood loss during surgery or due to an injury. Under hypovolemic conditions, a respiration-induced cyclical variation occurs in a plethysmograph baseline 340. In particular, the baseline 340 varies with a period corresponding to the respiration rate 350. This cyclical variation is particularly evident in patients undergoing positive ventilation. The amount of cyclical variation correlates to a person's blood volume, i.e. the less blood volume the greater the cyclical variation in the plethysmograph waveform. Accordingly, a measure of plethysmograph variation may be indicative of hypovolemic conditions.

Figure 4:
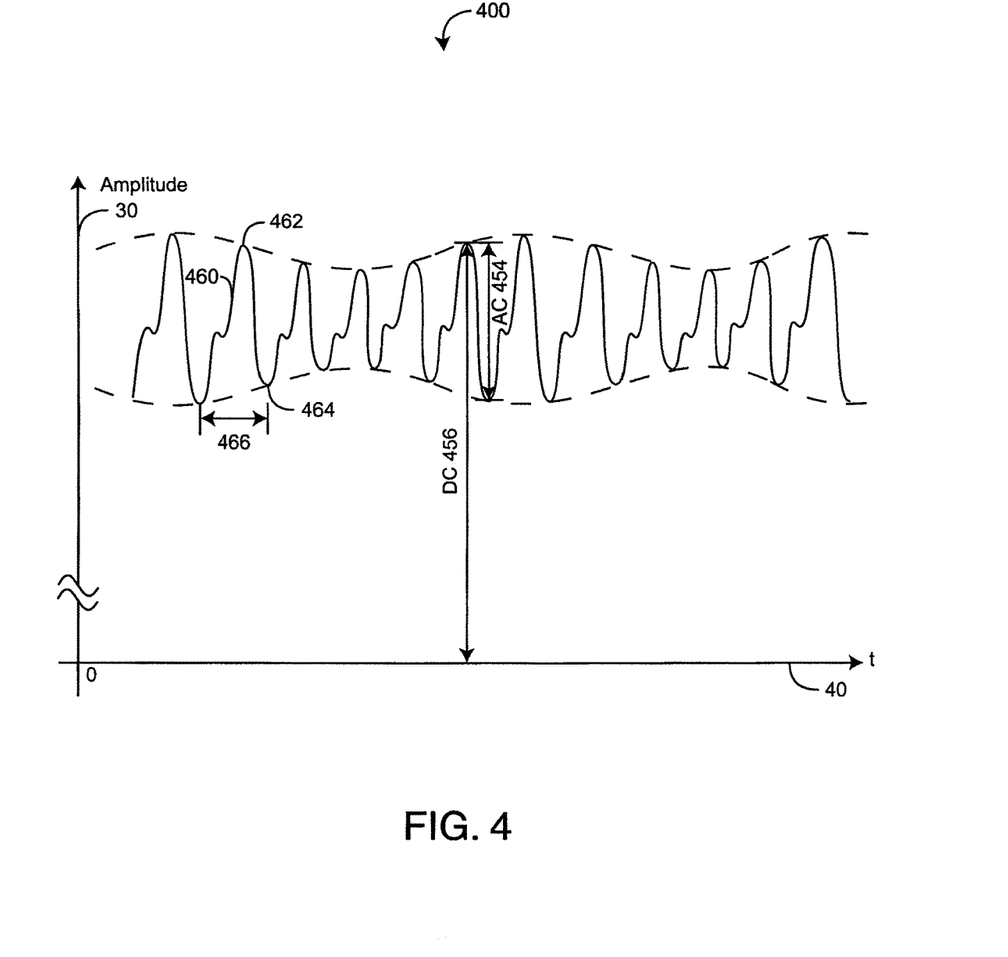
FIG. 4 is a plethysmograph illustrating measurement of a plethysmograph variability index (PVI)

FIG. 4 illustrates a plethysmograph 400 plotted on an amplitude axis 30 versus a time axis 40. As described above, the amplitude may be responsive to light absorption of pulsatile blood flow with a person's tissue. The plethysmograph 400 has multiple pulses 460 each with a peak 462 and a valley 464 and extending over a time period 466. A perfusion index (PI) value can be defined for each pulse 460:

$$PI = AC/DC \quad (1)$$

where "AC" 454 designates a peak amplitude 462 minus a valley amplitude 464 for a particular pulse and where "DC" 456 designates a peak amplitude 462 for a particular pulse. In an embodiment, an IR channel plethysmograph from a detector response to an IR wavelength LED is utilized to calculate PI. A plethysmograph variability index (PVI) is then calculated that is responsive to variations in perfusion index, as described below.

In an embodiment, PVI calculations utilize only PI values resulting from acceptable plethysmograph pulses. For example, a red channel plethysmograph responsive to a red wavelength LED is used to verify acceptable pulses in the IR channel. Physiological plethysmograph identification is disclosed in U.S. Pat. No. 7,044,918 titled Plethysmograph Pulse Recognition Processor, which is incorporated by reference herein. PVI values are calculated from a sorted and trimmed buffer representing a sliding time window of PI values. The sort orders the PI values from the minimum PI at one end of the buffer to the maximum PI at the other end of the buffer. A predetermined number of both maximum and minimum PIs are deleted from each end of the buffer and PVI is calculated as:

$$PVI=[(PI_{MAX}-PI_{MIN})/PI_{MAX}]\times 100 \qquad (2)$$

That is, PVI is the PI variation, expressed as a percentage of the difference between the maximum and minimum PIs remaining in the buffer. In an embodiment, a median PVI is calculated from PVIs stored in a second buffer. PVI is described in U.S. Provisional patent application No. 60/873,663 filed Dec. 09, 2006 titled Plethysmograph Variability Index, incorporated by reference herein. A PVI enabled physiological monitor advantageously provides a noninvasive numerical measure of hypovolemic conditions so as to titrate patient fluids.

DETAILED DESCRIPTION OF THE PREFERRED EMBODIMENT

Figure 5:
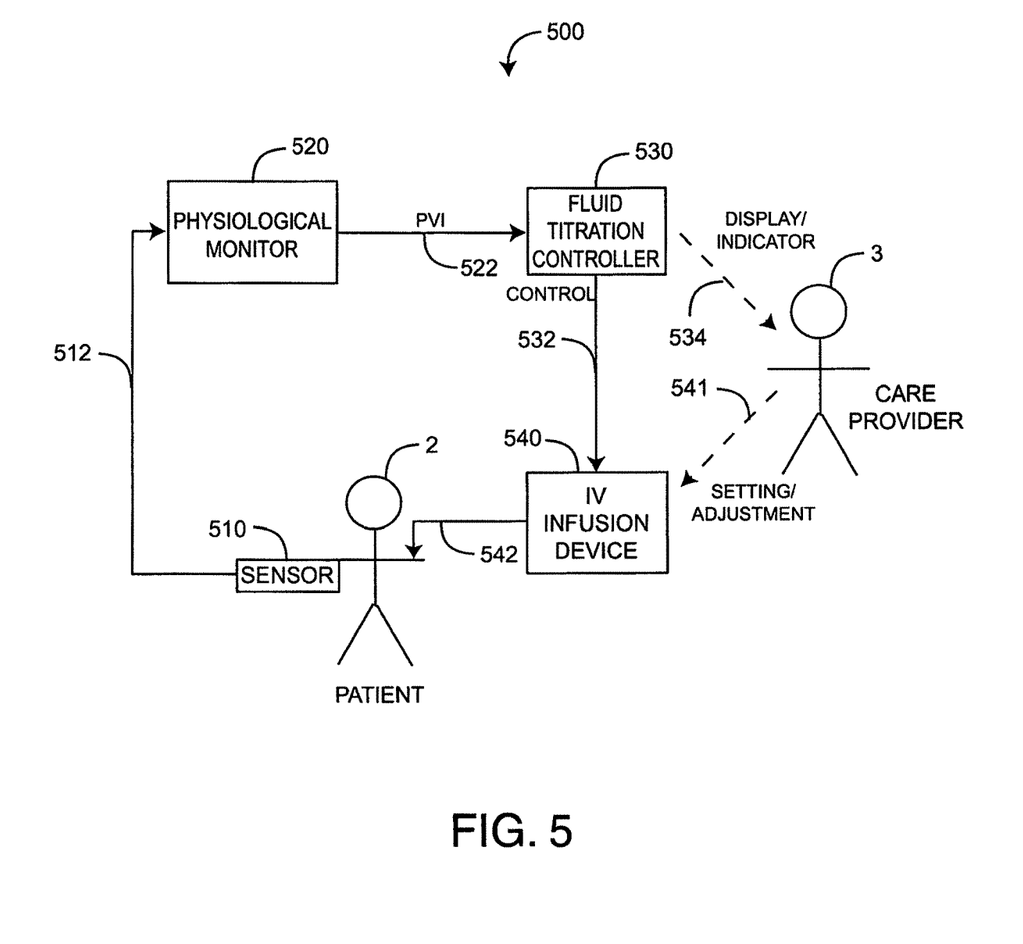
FIG. 5 is a general block diagram of an intravenous fluid titration system.

FIG. 5 illustrates a fluid titration system 500 having a sensor 510 attached to a person 2, a physiological monitor 520, a fluid titration controller 530 and an intravenous (IV) infusion device 540. Advantageously, the fluid titration system 500 utilizes a perfusion variability parameter, such as PVI described above, to regulate the administration of fluids to a person so as to control or prevent low blood volume or a hypovolemia. A noninvasive, optical sensor 510 allows a measure of tissue blood perfusion by detecting the absorption of sensor transmitted light by pulsatile blood flow within a tissue site, such as a finger, foot or ear to name a few. A sensor signal 512 responsive to that absorption is received and processed by the physiological monitor 520, which derives a plethysmograph variability index (PVI) or other measure of plethysmograph variability or, similarly, blood perfusion variability. A fluid titration controller 530 is responsive to PVI 522 and in particular to relatively large values of PVI indicating relatively large variations in perfusion index, a potential indicator of hypovolemia. The fluid titration controller 530, in turn, provides a control output 532 to an intravenous (IV) infusion device 540 so as to regulate circulating fluids and alleviate a hypovolemic condition in the person 2. The IV infusion device 540 administers a liquid solution, such as blood products or nutrient fluids injected directly into a vein (usually in the arm) at a prescribed rate over a period of time. In a closed-loop embodiment, the fluid titration controller 530 is responsive to PVI 522 or similar measure so as to start, control the rate of, or stop the infusion of fluids into the person 2. In an open-loop embodiment, the fluid titration controller 530 presents a display or other indicator 534 to a care provider 3 who manually inputs an adjustment or other setting 541 into the infusion device 540 so as to start, control the rate of, or stop the infusion of fluids into the person 2.

As shown in FIG. 5, the fluid titration controller 530 may be implemented in the physiological monitor 520, implemented in the IV infusion device 540, distributed between the physiological monitor 520 and the IV infusion device 540, or implemented as a standalone processing device. In an embodiment, the fluid titration controller 530 is a firmware process executed within the physiological monitor 520, as described with respect to FIG. 6, below. Physically, the physiological monitor 520 and the IV infusion device 540 may be separate units, as described with respect to FIG. 7, below, or combined into a single unit, as described with respect to FIG. 8, below.

Figure 6:
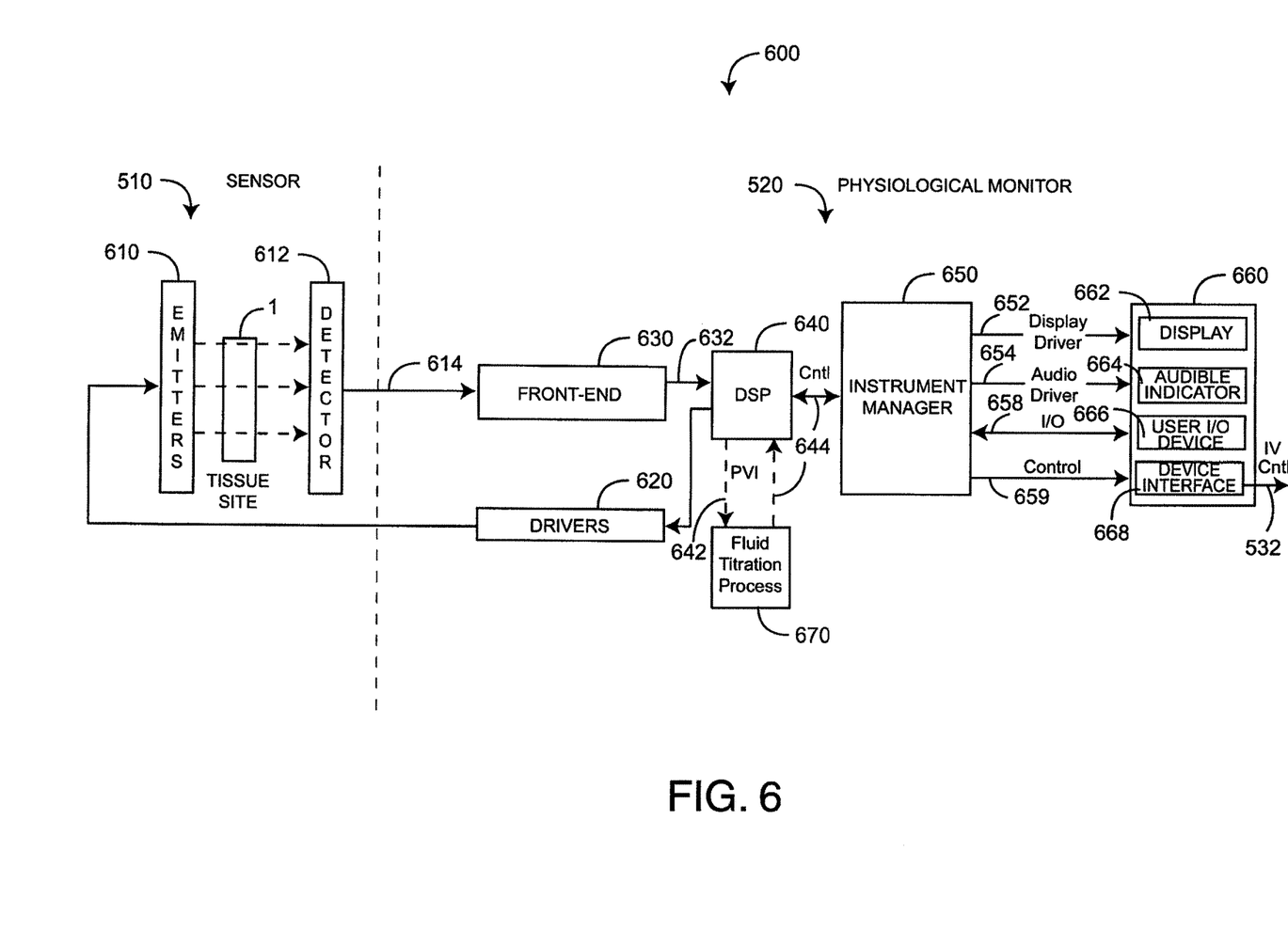
FIG. 6 is a general block diagram of a physiological monitoring system configured for a fluid titration application.

FIG. 6 illustrates a physiological monitoring system 600 capable of generating one or more blood parameter measurements such as oxygen saturation, perfusion index, carboxyhemoglobin and methemoglobin, to name a few. The monitoring system 600 has a sensor 510 and a physiological monitor 520. The sensor 510 attaches to a tissue site 1 and includes a plurality of emitters 610 capable of irradiating the tissue site 1 with various wavelengths of light, such as the red and infrared (IR) wavelengths utilized in pulse oximetry or multiple wavelengths different than or in addition to pulse oximetry wavelengths such as for measuring abnormal hemoglobin constituents. The sensor 510 also includes one or more detectors 612 capable of detecting the emitted light after attenuation by the tissue site 1.

As shown in FIG. 6, the physiological monitor 520 communicates with the sensor 510 to receive one or more intensity signals 614 responsive to one or more physiological parameters, then calculates and displays the parameter values. The physiological monitor 520 has drivers 620 that convert digital control signals into analog drive signals capable of driving the emitters 610. A front-end 630 converts composite analog intensity signal(s) 614 from the detector(s) 612 into digital data 632 input to a digital signal processor (DSP) 640. The input digital data 632 is referred to herein as a plethysmograph waveform or a "plethysmograph" for short. In an embodiment, the input digital data 632 is a multiplexed data stream including a red channel plethysmograph and an IR channel plethysmograph generated from alternate activation of red and IR wavelength emitters 610. The DSP 640 may comprise a wide variety of data and/or signal processors capable of executing processes in one or more of hardware, software and firmware for determining physiological parameters from the input data 632. In an embodiment, the DSP 640 generates PVI measurements 642 responsive to an IR channel plethysmograph portion of the digital data 632.

Also shown in FIG. 6, a fluid titration process, such as firmware executing on the DSP, inputs the PVI measurements 642 and generates control values 644 that are communicated directly or indirectly to an IV infusion device 540 (FIG. 5) so as to start, stop, continue or modify the infusion of fluids into a person 2 (FIG. 5). In an embodiment, the fluid titration process 670 is closed-loop and control values 644 are communicated to an IV infusion device 540 (FIG. 5) without human intervention. In an embodiment, the fluid titration process 670 is open-loop and control values 644 are communicated to a care provider 3 (FIG. 5) via a display 662, audible indicator 664 or other human interface device so that the care provider can manually adjust or provide settings for the IV infusion device 540 (FIG. 5) so as to regulate fluid infusion into the person 2 (FIG. 5).

Also shown in FIG. 6, the instrument manager 650 may comprise one or more microcontrollers controlling system management, such as monitoring the activity of the DSP 640 and communicating with I/O devices 660. In an embodiment, I/O devices 660 include one or more of a display 662, an audible indicator 664, a user input 666 and a device interface 688. A display 662 includes for example a readout, colored light or graphic generated by one or more of an LED, LCD, plasma screen or CRT, to name a few. An audible indicator 664 includes, for example, one or more of a speaker or other audio transducer. The user input device 666 may include, for example, one or more of a keypad, touch screen, pointing device, voice recognition device, or the like, or a network, computer or similar device that provides an external input capability.

Further shown in FIG. 6, the display 662, the audible indicator 664 or both in combination are capable of conveying information so that a caregiver 3 (FIG. 5) can manually adjust or otherwise provide inputs for a medical instrument, such as an IV infusion device 540 (FIG. 5), according to digital data 632 derived from an optical sensor 510 and processed by the DSP 640, the instrument manager 650 or both. For example, besides displaying indicia representative of calculated physiological parameters such as one or more of a pulse rate (PR), signal quality and values of blood constituents in body tissue, the display 662 is capable of guiding manual adjustment of an IV infusion device, such as by indicating a +, −, "on" and "off" to prompt a manual increase, decrease, stop or start of fluid flow.

In an embodiment, the instrument manager 650 provides a control signal 659 responsive to control values 644 calculated by the fluid titration firmware 670. The control signal 659 communicates with a device interface 668 so as to generate a corresponding IV infusion device control 532. For example, the instrument manager 360 converts PVI measurements 344 to a control signal 644 and transmits the control signal via the control port 659 to a device interface 668.

In an embodiment, an input port 658 responds to a user input device 666, such as a keypad, network, computer or similar device that provides an external interface. Using this interface, a caregiver 3 (FIG. 5) can initialize the instrument manager 650 with patient information, infusion device type and fluid type to name a few. During operation, the instrument manager converts the control values 644 to an appropriate control signal 659 according to the initialization information.

The fluid titration process 670 may be DSP firmware that executes a closed-loop algorithm for controlling an IV infusion device 540 based upon PVI or other measured plethysmograph or perfusion variability parameter. In an embodiment, the fluid titration process 670 triggers a control output 644 so as to disable fluid flow from the IV infusion device 540 if PVI falls below a predetermined threshold or otherwise reflects that hypovolemia may no longer be indicated for a patient 2 (FIG. 5). In an embodiment, the fluid titration process 670 triggers a control output 644 so as to enable fluid flow from the IV infusion device 540 if PVI increases above a predetermined threshold or otherwise reflects that hypovolemia may no longer be indicated for a patient 2 (FIG. 5). In an embodiment, the fluid titration process 670 modifies a control output 644 so as to adjust the rate of fluid flow or total administered amount of fluid flow from the IV infusion device 540 according to changes in PVI that reflect that hypovolemia may be decreasing or increasing in severity.

Figure 7:
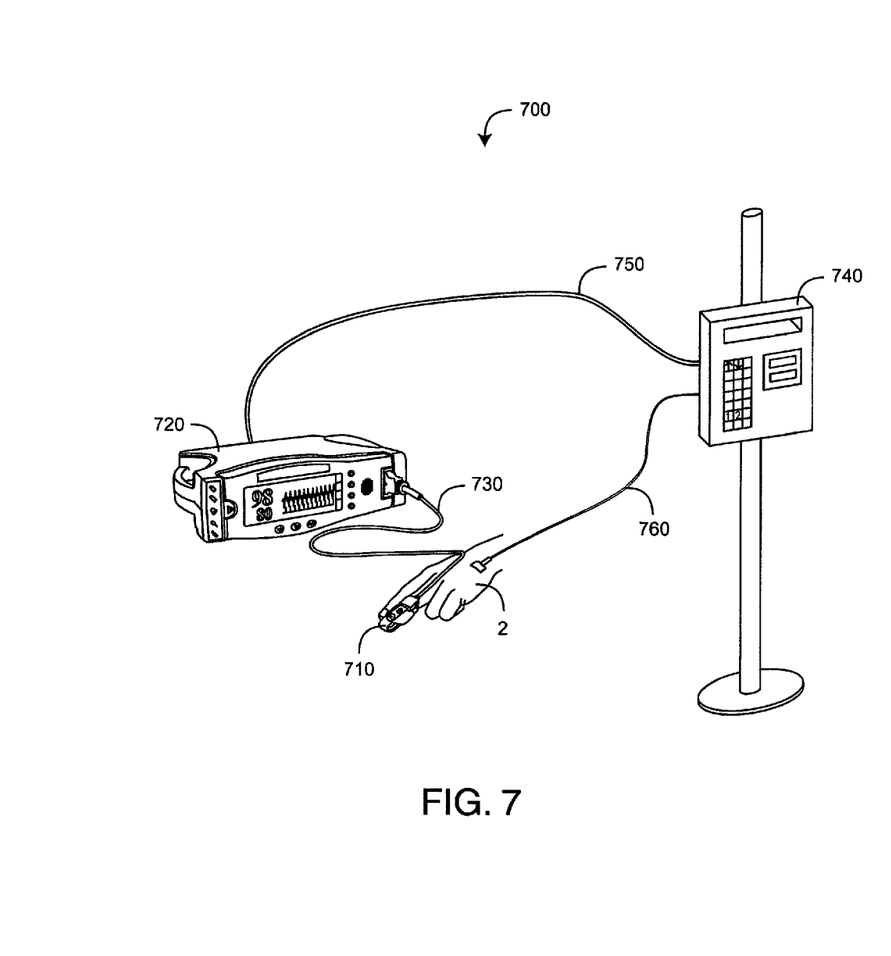
FIGS. 7-8 are illustrations of intravenous fluid titration system embodiments.

FIG. 7 illustrates a fluid titration system embodiment 700 having an optical sensor 710 attached to a person 2; a physiological monitor 720; a sensor cable 730 interconnecting the sensor 710 and monitor 720; an IV infusion device 740; a control cable 750 interconnecting the monitor 720 and infusion device 740; and an IV tube 760 also attached to the person 2. The optical sensor 710 provides a sensor signal via a sensor cable 730 to the physiological monitor 720. The physiological monitor 720 generates blood parameter measurements and processes those parameters to generate monitor and control outputs, as described with respect to FIGS. 5-6, above. In particular, the physiological monitor 720 generates control signals via a control cable 750 to the IV infusion device 740, which provides fluids to the person 2 via the IV tube 760.

Figure 8:
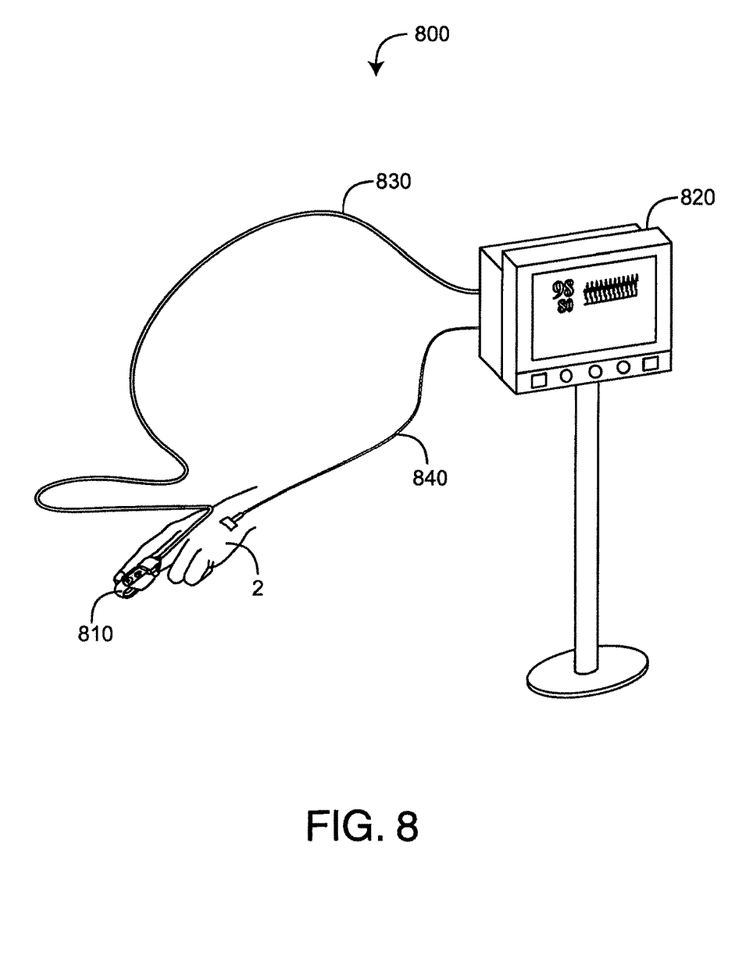

FIG. 8 illustrates another fluid titration system embodiment 800 having an optical sensor 810 and an IV tube 840 attached to a person 2 at one end and an integrated physiological monitor 820 at another end. The integrated physiological monitor 820 incorporates the functions of a physiological monitor 520 (FIG. 6) and an IV infusion device within a single unit or within physically connected units.

A fluid titration system has been disclosed in detail in connection with various embodiments. These embodiments are disclosed by way of examples only and are not to limit the scope of the claims that follow. One of ordinary skill in art will appreciate many variations and modifications.

What is claimed is:

1. A fluid titration system comprising:
   a noninvasive optical sensor including a light source configured to irradiate tissue of a monitored patient and one or more photodetectors configured to detect said light after attenuation by said tissue, said sensor outputting a signal responsive to said detected attenuated light, said signal including a pulsatile component responsive to variable absorption and a nonpulsatile component responsive to static absorption, said pulsatile component and said nonpulsatile component indicative of a blood volume in said patient;
   a physiological monitor configured to communicate with said sensor and receive said signal, said physiological monitor including a processor configured to process said signal to determine a measure of variability that depends at least on a ratio of said pulsatile component to said nonpulsatile component;
   a fluid titration controller configured to access said measure of variability and to output an infusion trigger when said measure of variability indicates a need for additional liquids by said patient; and
   a stand-alone infusion device configured to administer liquid solutions to said patient upon receipt of said infusion trigger, wherein said physiological monitor also houses said fluid titration controller.

2. The fluid titration system according to claim 1 wherein said fluid titration controller outputs said infusion trigger when said measure of variability indicates a blood volume decrease due to dehydration.

3. The fluid titration system according to claim 1 wherein said fluid titration controller outputs said infusion trigger when said measure of variability indicates a blood volume decrease due to hemorrhaging.

4. The fluid titration system according to claim 1 wherein said fluid titration controller outputs said infusion trigger when said measure of variability indicates a blood volume decrease due to a medical procedure being performed on said patient.

5. The fluid titration system according to claim 1 wherein said liquid solution comprises blood products.

6. The fluid titration system according to claim 1 wherein said liquid solution comprises nutrient fluids.

7. The fluid titration system according to claim 1 wherein said processor is configured to determine said measure of variability from at least a change in the ratio of said pulsatile component to said nonpulsatile component.

8. The fluid titration system according to claim 1 wherein said measure of variability comprises a measure of perfusion index variability.

9. A method of managing a blood volume of a monitored patient, the method comprising:
noninvasively detecting, with a detector of a noninvasive sensor, light attenuated by tissue of said monitored patient at a measurement site;
electronically determining, with a signal processor, a measure of variability depending at least on a ratio of a pulsatile component to a nonpulsatile component of a signal that is responsive to said detected light, said pulsatile component and said nonpulsatile component indicative of a blood volume in said tissue, said pulsatile component responsive to variable absorption and said nonpulsatile component responsive to static absorption;
electronically determining, with said signal processor, whether said measure of variability indicates a need for said monitored patient to receive additional liquid solutions;
electronically triggering a stand-alone infusion device when said determining indicates said need, wherein said triggering comprises generating with an oximeter an infusion device trigger signal; and
administering, with said stand-alone infusion device, liquid solutions when said infusion device is triggered.

10. The method according to claim 9 wherein said administering comprises electronically administering with said infusion device.

11. The method according to claim 9 wherein said electronically determining said measure of variability comprises electronically processing a respiration-induced cyclical variation in said signal.

12. The method according to claim 9 wherein said measure of variability is responsive to a dehydration condition of said patient.

13. The method according to claim 9 wherein said measure of variability is responsive to a hemorrhaging condition of said patient.

14. The method according to claim 9 wherein said electronically determining said measure of variability comprises processing signals responsive to said detected light with said oximeter.

15. The method according to claim 9 wherein said electronically determining whether said measure of variability indicates said need comprises electronically comparing said measure of variability with a predetermined threshold.

16. The method according to claim 9 wherein said electronically determining said measure of variability comprises electronically determining said measure of variability from at least a change in the ratio of said pulsatile component to said nonpulsatile component.

17. The method according to claim 9 wherein said measure of variability comprises a measure of perfusion index variability.

18. A patient monitoring system comprising:
a noninvasive optical sensor including a light source configured to irradiate tissue of a monitored patient and one or more photodetectors configured to detect said light after attenuation by said tissue, said sensor outputting a signal responsive to said detected attenuated light, said signal including a pulsatile component responsive to variable absorption and a nonpulsatile component responsive to static absorption, said pulsatile component and said nonpulsatile component indicative of a blood volume in said patient;
a physiological monitor configured to communicate with said sensor and receive said signal, said physiological monitor including a processor configured to process said signal to determine a measure of variability that depends at least on a ratio of said pulsatile component to said nonpulsatile component; and
a fluid titration controller configured to access said measure of variability and to output an infusion indication when said measure of variability indicates a need for additional liquids by said patient, said infusion indication guiding adjustment of administration of liquid solutions to said patient with a stand-alone infusion device configured to administer said liquid solutions to said patient, wherein said physiological monitor also houses said fluid titration controller.

19. The patient monitoring system according to claim 18 wherein said infusion indication comprises an audible or visual indication and guides manual adjustment of administration of liquid solutions to said patient with said stand-alone infusion device.

20. The patient monitoring system according to claim 18 wherein said fluid titration controller is configured to output said infusion indication to automatically control administration of liquid solutions to said patient with said stand-alone infusion device.

* * * * *